United States Patent
Witteler

[11] Patent Number: 6,077,918
[45] Date of Patent: Jun. 20, 2000

[54] POLYARYLENE SULPHIDES WITH POLYMER-BOUND PHOSPHONIUM SALTS AND PROCESS FOR PRODUCING THEM

[75] Inventor: Helmut Witteler, Frankfurt, Germany

[73] Assignee: Hoechst Aktiengesellschaft, Frankfurt, Germany

[21] Appl. No.: 08/973,638

[22] PCT Filed: Jun. 17, 1996

[86] PCT No.: PCT/EP96/02609

§ 371 Date: Dec. 23, 1997

§ 102(e) Date: Dec. 23, 1997

[87] PCT Pub. No.: WO97/02308

PCT Pub. Date: Jan. 23, 1997

[30] Foreign Application Priority Data

Jun. 30, 1995 [DE] Germany .............. 195 23 861
Dec. 15, 1995 [DE] Germany .............. 195 46 912

[51] Int. Cl.[7] .................... C08G 75/14; C08G 75/18; C08G 75/20
[52] U.S. Cl. .................... 525/537; 528/388; 525/535
[58] Field of Search .................... 525/537, 535; 528/388

[56] References Cited

FOREIGN PATENT DOCUMENTS

| | | |
|---|---|---|
| 3136255 A1 | 3/1983 | Germany . |
| 3086704 | 4/1991 | Japan . |
| WO 94/10214 | 5/1994 | WIPO . |

*Primary Examiner*—Patricia A. Short
*Attorney, Agent, or Firm*—Frommer Lawrence & Haug LLP

[57] ABSTRACT

Phosphonium ionomers which, as random copolymers, are composed of the units (1) and (2)

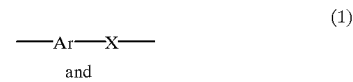

and

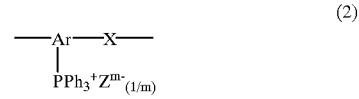

in which
Ar— is a phenylene radical or a biphenylene, naphthylene or anthrylene radical or another divalent aromatic radical and may be different units within the polymer chain;
—X— is an —S—, —SO— and/or —SO$_2$— unit,
where —X— within the polymer chain may be up to 3 different units;
Z is a monovalent or polyvalent opposite ion;
Ph is a phenyl radical;
m is the charge of the opposite ion
and the average degree of polymerization is in the range from 3 to 2000.

The polymers can be used for the production of membranes, in particular for electrochemical cells.

21 Claims, No Drawings

POLYARYLENE SULPHIDES WITH POLYMER-BOUND PHOSPHONIUM SALTS AND PROCESS FOR PRODUCING THEM

The invention relates to polyarylene sulfides, sulfoxides and sulfones which are substituted by triphenylphosphonium groups, a process for the preparation of these compounds and their use for the production of membranes.

Polymer-bound tetraalkylphosphonium salts are of considerable interest for the production of ion exchangers (U.S. Pat. No. 4,043,948), phase-transfer catalysts (Tomoi et al., J. Am. Chem. Soc. 103, 3821–3828 (1981)) and their use as biocides (Endo et al., J. Appl. Polymer Sci., 52, 641–447 (1994)).

Thermally more stable than tetraalkylphosphonium salts are the corresponding tetraarylphosphonium salts (Houben-Weyl Vol. 12/1, page 47). For applications in which high thermal stability is required, the use of tetraarylphosphonium salts is therefore preferable to the use of alkylphosphonium salts. For this purpose, the substrate polymer, too, must have sufficiently high thermal stability. This is the case with polyarylene sulfides and their oxidation products having sulfoxide groups and sulfonyl groups, for example poly(1,4-phenylene sulfide).

Tetraarylphosphonium salts are generally prepared from the corresponding aryl halide and triphenylphosphine, catalytically active transition metals being used (Houben Weyl Vol. E1, pages 518–525). Furthermore, dehydroaromatics, diaryliodonium salts or quinones may also be used as starting materials, in addition to aryl halides.

Tetraarylphosphonium tetraphenylborates bound to isobutylene polymers, rubber, neoprene or polyethylene are described in PCT/US 93/10027. Here, the corresponding phosphine is reacted with a halogenated polymer and an alkali metal borate in toluene or tetrahydrofuran.

The phosphonium salts known to date have the disadvantage that they are either chemically and thermally unstable, in particular when an aliphatic radical is attached to the phosphorus, or are insoluble in the conventional solvents. Furthermore, their preparation is in general possible only with considerable technical complexity and is therefore uneconomical.

It was therefore the object of the invention to provide soluble, thermally and chemically stable phosphonium ionomers which can be prepared in a simple and economical manner.

The present invention achieves this object and relates to polymeric phosphonium ionomers which, as random copolymers, are composed of the units (1) and (2)

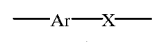
(1)

and

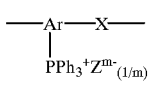
(2)

in which

Ar— is a phenylene radical, in particular a 1,3- or 1,4-phenylene radical, or a biphenylene, naphthylene or anthrylene radical or another divalent aromatic radical and may be different units within the polymer chain;

—X— is an —S—, —SO— and/or —SO$_2$— unit, where —X— within the polymer chain may be up to 3 different units;

Z is a monovalent or polyvalent opposite ion;

Ph is a phenyl radical;

m is the charge of the opposite ion and the average degree of polymerization, i.e. the average number of all units (1) and (2) in a polymer chain, is in the range from 3 to 2000, preferably in the range from 100 to 1000.

The average proportion of units (2) in the polymer is in the range from 0 to 100 mol %, preferably in the range from 5 to 95 mol %.

The polymer may, if desired, be crosslinked via —X—, —Ar— and/or —X—Ar—X units.

Ar is in particular a 1,4-phenylene or a 1,4- and a 1,3-phenylene radical.

In the phosphonium ionomer according to the invention, Z is, for example, at least one ion selected from the following group: $CO_3^{2-}$, $CN^-$, $OCN^-$, $Hal^-$ in particular $Br^-$, $Cl^-$, $I^-$, $OH^-$, $NO_3^-$, $SO_3^{2-}$, $SO_2^{2-}$ or $SCN^-$. In particular Z is $Br^-$, $Cl^-$, $I^-$ or $OH^-$.

Some of the Ar units, preferably from 5 to 50%, may furthermore be substituted by bromine.

The average molecular weight of the triphenylphosphonium-polyarylene sulfide according to the invention is in the range from 4000 to 300,000 g/mol, in particular in the range from 30,000 to 200,000.

In a preferred embodiment, either all Ar units may carry at least one triphenylphosphonium group $PPh_3^+Z^{m-}_{(1/m)}$ as substituent or some Ar units carry two triphenylphosphonium groups $PPh_3^+Z^{m-}_{(1/m)}$ as a substituent, the remaining Ar units carrying only one or no $PPh_3^+Z^{m-}_{(1/m)}$ group as a substituent.

In a preferred embodiment, Ar is a 1,3- or 1,4-phenylene unit. In this case, X is a sulfur bridge —S— and/or a unit —SO— and/or a unit —SO$_2$—. In a particular embodiment, —X— may also be —O— in addition to the stated groups, —X— in the polymer chain being up to four different units.

In a preferred embodiment, —X— in the ionomers according to the invention is the units —SO$_2$— and —O— in equal stoichiometric amounts and —Ar— is a 1,4-phenylene unit or a 1,4-phenylene unit and a di(4,4'-phenylene)-2,2'-propane unit in equal proportions.

The —S— units of the ionomer according to the invention may subsequently be converted into —SO— or —SO$_2$— units, it being possible for —X— units to be present both as —S— and —SO— units side by side and as —S— and —SO$_2$— units or as —S—, —SO— and —SO$_2$— units within the same polymer.

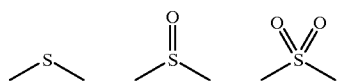

According to the following formula, —S— is sulfide, —SO— is sulfoxide and —SO$_2$— is sulfonyl.

For the preparation of the ionomers according to the invention, a brominated polyarylene sulfide (U.S. Pat. No. 4,064,115, DE-A-3 136 255) is reacted with triphenylphosphine in the presence of a transition metal halide, preferably of a nickel, cobalt, zinc or copper halide, in a polar aprotic liquid which can also serve as a solvent, or without further additives (i.e. in the absence of a solvent), at a temperature in the range from 140 to 240° C., in particular from 190 to 220° C. Here, the reaction batch may be present both as a one-phase system and as a two-phase system. In a preferred embodiment, the starting polymer used is brominated poly (1,4-phenylene sulfide) in which from 10 to 120% of the repeating units are substituted by bromine. According to the invention, from 10 to 100% of the Br units of the polyarylene sulfide are replaced by triphenylphosphine units (PPh$_3^+$) and simultaneously from 0 to 50% of the Br units are replaced by hydrogen. In particular, from 10 to 50% of the Br units are replaced by triphenylphosphine units and simultaneously from 10 to 50% are replaced by hydrogen.

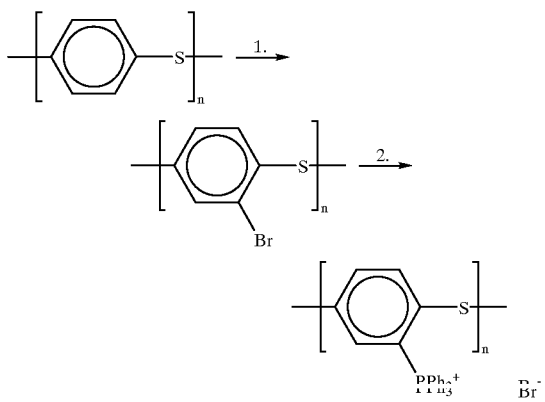

The reaction time is in general from 0.5 to 24 hours, preferably from 3 to 8 hours. Thereafter, the water/solvent azeotropic mixture is distilled off and the reaction mixture is poured into an excess of a liquid which is a solvent for the triphenylphosphine and a precipitating agent for the phosphonium ionomer. The precipitated polymer is filtered off and washed.

Transition metal halides which are used in the process according to the invention are, for example, nickel, cobalt, zinc or copper halides or hydrates of these compounds, such as, for example, nickel(II) bromide hexahydrate.

Suitable polar aprotic liquids are, for example, nitrobenzene, dimethylformamide, dimethyl sulfoxide and benzonitrile.

The stoichiometric metal halide/triphenylphosphine ratio is from 0.001 to 1.0, in particular from 0.05 to 0.5. In general, from 0.2 to 10 equivalents of triphenylphosphine are used per monobrominated phenylene unit.

According to the invention, the concentration of the triphenylphosphine is in particular in the range from 0.1 to 10.0 mol/l, based on the polar aprotic liquid.

Liquids which, according to the process according to the invention, can be used for precipitating the resulting phosphonium ionomer are, for example, $C_1$–$C_8$—alcohols, acetone and toluene, preferably methanol or other liquids in which the compounds according to the invention are insoluble.

In a further preferred embodiment, the claimed compounds are obtainable by reacting a brominated polyarylene sulfide with triphenylphosphine in the presence of a transition metal halide and of an alkylmagnesium halide. Solvents used are in general ethers, such as, for example, diethyl ether or tetrahydrofuran. The reaction mixture is heated for from 0.5 to 24, preferably from 2 to 6, hours at a temperature in the range from 30 to 1 00° C., in particular from 40 to 70° C., preferably with refluxing of the relevant solvent. In a preferred variant, the heating of the reaction mixture may be preceded by a reaction period of from 5 to 120 minutes at room temperature.

The stoichiometric ratio of triphenylphosphine to brominated phenylene units of the polymer is from 0.2 to 10 equivalents, preferably from 1.0 to 3.0 equivalents.

The stoichiometric ratio of the transition metal salt to triphenylphosphine is in the range from 0.005 to 0.2, in particular in the range from 0.03 to 0.1. The concentration of triphenylphosphine is from 0.05 to 5.0 mol/l, preferably from 0.1 to 2.0 mol/l, based on the solvent.

Alkylmagnesium halides used are the conventional Grignard reagents, preferably ethylmagnesium halide.

To terminate the reaction, a small amount of a dilute mineral acid is added. A 2N mineral acid, for example hydrochloric acid or sulfuric acid, is preferably used, the added volume being from 1/10 to 1/5 of the solvent volume.

Finally, the reaction mixture is poured into an excess of a liquid which is a solvent for the triphenylphosphine and a nonsolvent for the polymeric reaction product. Suitable nonsolvents for the polymer are the abovementioned liquids. The polymer is filtered off and washed.

In order further to increase the thermal stability of the phosphonium ionomers according to the invention, in particular in the hydroxide form, said ionomers can either be exposed to an ozone stream, in particular having a concentration of from 0.5 to 200 g/m$^3$, preferably from 5 to 50 g/m$^3$, or be treated with a dilute solution of hydroperoxides or with HNO$_3$, in particular having a hydrogen peroxide concentration of from 3 to 30%.

Depending on the reaction conditions, the —S— units of the polymer are oxidized to —SO—, preferably with $H_2O_2$ or HNO$_3$, or to —SO$_2$— units, in particular with ozone. This results in an increase in the stability of the neighboring phosphorus-carbon bond. Furthermore, the oxidation to the sulfoxide (—SO—) and to the sulfone (—SO$_2$—) also results in an increase in the stability of the —S— bridge, in particular to attack by acids.

The opposite ion Z, which is halogen when transition metal halides are used, can be exchanged for any desired other opposite ions, e.g. $CO_3^{2-}$, $CN^-$, $OCN^-$, $OH^-$, $NO_3^-$, $SO_3^{2-}$, $SO_2^{2-}$ or $SCN^-$, via ion exchange by the known technical methods.

The phosphonium ionomers according to the invention, or solutions or dispersions of these polymers in fluids, in particular in solvents in which the ionomers are soluble or partially soluble, can be used, for example, as bactericides or for the production of membranes, in particular for membranes which are used for filtering gases and liquids, for dialysis, osmosis, reverse osmosis and pervaporation.

A further potential use of the ionomers described and of membranes of this material is the use as anion exchangers and their use in electrochemical cells, in particular in electrodialysis cells as an anion exchange membrane or part of a bipolar membrane.

EXAMPLES

TABLE 1

Bromination of polyphenylene sulfide (PPS)

| Example | Starting materials | Reaction procedure | Yield | Elemental analysis | Degree of substitution (Br) | Solubility | GPC (PS equivalents) $M_W/M_N$ |
|---|---|---|---|---|---|---|---|
| 1 | 47 mmol PPS<br>12 mmol $Br_2$ | $N_2/Br_2$ stream | 6.05 g | $C_{6.00}H_{3.92}S_{1.00}Br_{0.06}$ | 6% | | |
| 2 | 93 mmol PPS<br>93 mmol $Br_2$ | $N_2/Br_2$ stream | 12.5 g | $C_{6.00}H_{4.01}S_{0.97}Br_{0.22}$ | 22% | | |
| 3 | 46 mmol PPS<br>230 mmol $Br_2$<br>40 ml $CHCl_3$ | Suspension | 3.8 g | $C_{6.00}H_{3.76}S_{0.96}Br_{0.77}$ | 77% | | |
| 4 | | $CHCl_3$ extract from Example 3 | 1.1 g | $C_{6.00}H_{3.55}S_{0.94}Br_{1.18}$ | 118% | soluble ($CHCl_3$) | 1850/1130 |
| 5 | 460 mmol PPS<br>521 mmol $Br_2$<br>100 ml $CHCl_3$ | Suspension | 55.1 g<br>20.6 g | $C_{6.00}H_{3.75}S_{0.94}Br_{0.72}$<br>$C_{6.00}H_{3.61}S_{0.95}Br_{0.95}$ | 72%<br>95% | insoluble<br>soluble ($CHCl_3$) | 4400/2600 |
| 6 | 46 mmol PPS<br>46 mmol $Br_2$<br>20 ml $CHCl_3$ | Suspension | 3.7 g | $(C_{6.00}H_{2.63}S_{0.53}Br_{1.25})$ | | | |

Phosphonium salts of brominated PPS

Example 7

A mixture of 1.2 g of brominated poly(1,4-phenylene sulfide) (37% of the repeating units are monobrominated), 100 g of triphenylphosphine, 0.87 g of nickel bromide hexahydrate and 15 ml of benzonitrile is heated to 210° C. over 8 hours. It is then cooled to 100° C. and the reaction mixture is added to 1000 ml of methanol. The crude product is filtered off with suction and washed with methanol. A poly(1,4-phenylene sulfide) in which 13% of the repeating units are substituted by —$PPh_3^+Br^-$ groups is obtained

TABLE 2

| Example | Starting material | Reaction conditions | Yield[1] | Elemental analysis | Degree of substitution (P) | Solubility |
|---|---|---|---|---|---|---|
| 8 | 40 mmol (5.0 g) of product from Example 2<br>40 mmol $PPh_3$<br>19 mmol $NiBr_2 \cdot 6H_2O$<br>50 ml benzonitrile | 4 h/195° C. | 5.16 g | $C_{7.32}H_{5.90}S_{1.00}P_{0.03}Br_{0.04}(O_{0.54})$ | 3% | |
| 9 | 8.9 mmol (1.5 g) of product from Example 3<br>16 mmol $PPh_3$<br>3.7 mmol $NiBr_2 \cdot 6H_2O$<br>30 ml benzonitrile | 12 h/190° C.<br>5 h/210° C. | 0.72 g | $C_{7.90}H_{5.29}S_{1.00}P_{0.12}Br_{0.11}(O_{0.47})$<br>ESCA:<br>$C_{8.84}(H_x)S_{1.00}P_{0.17}Br_{0.08}O_{0.33}$ | 12%<br>17% | partially soluble (NMP, DMSO) |
| 10 | 7.1 mmol (1.2 g) of product from Example 3<br>38 mmol $PPh_3$<br>3.7 mmol $NiBr_2 \cdot 6H_2O$<br>30 ml benzonitrile | 13 h/210° C. | 0.39 g | $C_{7.50}H_{4.85}S_{1.00}P_{0.12}Br_{0.21}(O_{0.30})$ | 12% | partially soluble (NMP, DMSO) |
| 11 | 8.9 mmol (5.0 g) of product from Example 3<br>16 mmol $PPh_3$<br>3.7 mmol $NiBr_2 \cdot 6H_2O$<br>30 ml benzonitrile | 15 h/220° C. | 2.05 g | $C_{10.5}H_{8.22}S_{1.00}P_{0.22}Br_{0.22}(O_{0.38})$ | 22% | partially soluble (NMP, DMSO) |
| 12 | 25 mmol (5.0 g) of product from Example 4<br>54 mmol $PPh_3$<br>12 mmol $NiBr_2 \cdot 6H_2O$<br>25 ml benzonitrile | 6 h/210° C.<br>8 h/215° C. | 1.27 g | $C_{13.6}H_{9.94}S_{1.00}P_{0.38}Br_{0.92} \cdot 0.54$ NMP | 38% | partially soluble (NMP) |

[1] methanol-insoluble fraction.

The reaction products from Examples 8 to 12 are insoluble in water. "Partially soluble" means that 1 g of polymer undergoes at least 80% solution in 20 g of solvent.

Example 13

A poly(1,4-phenylene sulfide) in which 13% of the repeating units are substituted by $PPh_3^+Br^-$ groups is gassed for 10 minutes with ozone (50 g/cm³, carrier gas oxygen, commercial ozone generator of Fischer, Meckendorf). As a result, all sulfur bridges R—S—R of the polymer are oxidized to R—$SO_2$—R.

The examples were worked out with poly(1,4-phenylene sulfide) Fortron™ (type 300 B0) (Hoechst AG, Fortron Group).

I claim:

1. A phosphonium ionomer which, as random copolymers, is composed of the units

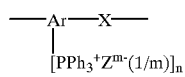

where
- Ar is a phenylene radical or a biphenylene, naphthylene radical, anthrylene or another divalent aromatic radical and may be different units within the polymer chain;
- X is an —S—, —SO— and/or —$SO_2$— unit, and optionally may further be an —O— unit, in addition to said —S—, —SO— and/or —$SO_2$ units where —X—, within the polymer chain may be up to 3 different units;
- Z is a monovalent or polyvalent opposite ion;
- Ph is a phenyl radical;
- m is the charge of the opposite ion
- n is 1 or 2; and
the average degree of polymerization is in the range from 3 to 2000.

2. A phosphonium ionomer as claimed in claim 1, wherein Z is at least one ion selected from the following group: $CO_3^{2-}$, $CN^-$, $OCN^-$, $Hal^-$, $OH^-$, $NO_3^-$, $SO_3^{2-}$, $SO_2^{2-}$ and $SCN^-$.

3. A phosphonium ionomer as claimed in claim 1, wherein 5–50% of the Ar units are substituted by bromine.

4. A phosphonium ionomer as claimed in claim 1, which has an average molecular weight in the range from 4000 to 300,000 g/mol.

5. A phosphonium ionomer as claimed in claim 1, wherein all Ar units carry at least one triphenylphosphonium group $PPh_3^+Z^{m-}_{(1/m)}$ as substituent.

6. A phosphonium ionomer as claimed in claim 1, wherein, within the ionomer, —X— is an —S— and —SO— unit, an —S— and —$SO_2$— unit, an —SO— and —$SO_2$— unit or an —S—, —SO— and —$SO_2$— unit.

7. A phosphonium ionomer as claimed in claim 1, wherein —X— is an —$SO_2$— and an —O— unit in equal stoichiometric amounts and —Ar— is a 1,4-phenylene unit or a 1,4-phenylene unit and a di(4,4'-phenylene)-2,2'-propane unit in equal proportions.

8. A phosphonium ionomer as claimed in claim 1, wherein the polymer is crosslinked via —X—, —Ar— and/or —X—Ar—X— units.

9. A phosphonium ionomer as claimed in claim 1 wherein n is 1.

10. A process for preparing a phosphonium ionomer according to claim 1, which comprises reacting a brominated polyarylene sulfide and triphenylphosphine in the presence of a transition metal halide and a protic apolar liquid.

11. The process as claimed in claim 10, wherein from 10 to 100% of the Br units of the polyarylene sulfide are replaced by $PPh_3^+$ units.

12. The process as claimed in claim 10, wherein the stoichiometric ratio of the metal halide to triphenylphosphine is in the range from 0.1 to 2.0.

13. The process as claimed in claim 10, wherein from 0.2 to 10 equivalents of triphenylphosphine are used per brominated phenylene unit.

14. The process as claimed in claim 10, wherein the reaction temperature is in the range from 140 to 240° C.

15. The process as claimed in claim 10, wherein the phosphonium ionomer obtained is oxidized in a subsequent step, the —S— bridges being converted into —SO— and/or —$SO_2$— units.

16. A solution or dispersion of a polymer as claimed in claim 1 in a fluid.

17. A membrane containing a polymer as claimed in claim 1, wherein the said membrane is used for filtering gases and liquids, for dialysis, osmosis, reverse osmosis and pervaporation.

18. A method of killing bacteria which comprises filtering a liquid or gas containing said bacteria with a polymer according to claim 1.

19. An anion exchanger which comprises a membrane containing a polymer according to claim 1.

20. An electrochemical or electrodialysis cell which comprise a membrane containing a polymer according to claim 1.

21. In a process for preparing a membrane, the improvement which comprises adding a polymer according to claim 1 to said process.

* * * * *